United States Patent
Notté et al.

(10) Patent No.: US 9,315,528 B2
(45) Date of Patent: *Apr. 19, 2016

(54) METHOD FOR THE MANUFACTURE OF PHOSPHONOALKYL IMINODIACETIC ACID

(75) Inventors: Patrick Notté, Wavre (BE); David Lemin, Brussels (BE); Cedric Nicolas Pirard, Bolland (BE)

(73) Assignee: Straitmark Holding AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/502,502

(22) PCT Filed: Oct. 27, 2010

(86) PCT No.: PCT/EP2010/066210
§ 371 (c)(1),
(2), (4) Date: Jun. 29, 2012

(87) PCT Pub. No.: WO2011/051309
PCT Pub. Date: May 5, 2011

(65) Prior Publication Data
US 2013/0102808 A1   Apr. 25, 2013

(30) Foreign Application Priority Data
Oct. 27, 2009   (EP) .................................... 09174206

(51) Int. Cl.
*C07F 9/38*   (2006.01)
(52) U.S. Cl.
CPC .................................... *C07F 9/3808* (2013.01)
(58) Field of Classification Search
None
See application file for complete search history.

(56) References Cited

U.S. PATENT DOCUMENTS

| 3,288,846 A | 11/1966 | Riyad et al. |
|---|---|---|
| 4,775,498 A * | 10/1988 | Gentilcore ...................... 562/17 |
| 5,208,000 A * | 5/1993 | Yang et al. .................. 423/316 |
| 5,527,953 A * | 6/1996 | Jones et al. ...................... 562/17 |
| 6,130,351 A | 10/2000 | Stern et al. |
| 6,232,494 B1 | 5/2001 | Morgenstern et al. |
| 2002/0148786 A1 | 10/2002 | Phillips |

FOREIGN PATENT DOCUMENTS

| CN | 101284847 | 10/2008 |
|---|---|---|
| CN | 101307074 | 11/2008 |
| CN | 101348266 | 1/2009 |
| EP | 0595598 A | 4/1994 |
| EP | 0618212 A | 5/1994 |
| EP | 0618212 | * 10/1994 |
| GB | 2154589 | 9/1985 |
| WO | 94/15939 | 7/1994 |
| WO | 96/40698 | 12/1996 |
| WO | 00/59915 | 10/2000 |
| WO | 2009/130322 | 10/2009 |
| WO | 2009130322 | * 10/2009 |

* cited by examiner

*Primary Examiner* — Karl J Puttlitz
(74) *Attorney, Agent, or Firm* — Husch Blackwell LLP

(57) ABSTRACT

An improved method for the manufacture of phosphonoalkyl iminodiacetic acid $M_2PO_3$—X—N—$(CH_2COOM)_2$ wherein X is a $C_{1-6}$ linear or branched alkyl group; and M is selected from hydrogen, alkali, earth-alkali, ammonium and protonated amine is disclosed. The iminodiacetic acid starting material is reacted with a substantially stoichiometric amount of phosphorous acid, in the presence of a large excess of phosphoric acid to thereby yield a reaction medium insoluble reaction product (PAI-DA) which can be separated from the reaction medium. In a particularly preferred approach, the phosphorous acid is prepared in situ starting from liquid $P_4O_6$.

13 Claims, No Drawings

METHOD FOR THE MANUFACTURE OF PHOSPHONOALKYL IMINODIACETIC ACID

CROSS REFERENCE TO RELATED APPLICATIONS

This Application is a U.S. National Phase patent application of International Application PCT/EP2010/066210, filed 27 Oct. 2010, which claims the benefit of priority from European Patent Application No. 09174206.4 filed on 27 Oct. 2009. The disclosures of International Application PCT Application No. PCT/EP2010/066210 and European Patent Application No. 09174206.4 are incorporated herein by reference.

This invention pertains to a method for the manufacture of a phosphonoalkyl iminodiacetic acid (PAIDA), in particular phosphonomethyl iminodiacetic acid (PMIDA) component, a major intermediate used in preparing glyphosate, also known as N-phosphonomethylglycine. The iminodiacetic acid (IDA) starting component is reacted with phosphorous acid and formaldehyde in the presence of phosphoric acid. The phosphorous acid is used in stoichiometric level required for the synthesis of the phosphonomethyl iminodiacetic acid compound. The reaction is conducted in the presence of a substantial level of phosphoric acid, in particular in a level such that the molar ratio of phosphoric:phosphorous is from 9:0.8 to 1:1. It was found that, within the context of the claimed technology, the reaction product, predominantly the phosphonoalkyl iminodiacetic acid, is substantially reaction medium insoluble and can be separated and recovered routinely. In a particularly preferred and major embodiment, the phosphorous acid reactant is prepared in situ by the hydrolysis of liquid $P_4O_6$ in the reaction medium.

The glyphosate chemistry, including the art relating to intermediates, methods of manufacture and so on, has been used commercially for a long time and is accordingly eminently well known in the relevant domain.

U.S. Pat. No. 3,288,846 discloses a process for preparing aminoalkylenephosphonic acids by forming an aqueous mixture having a pH below about 4 containing a nitrogenous material selected from the group consisting of ammonia, primary amines, and secondary amines; an organic carbonyl compound selected from the group consisting of aldehydes and ketones; and orthophosphorous acid, and subjecting said mixture to temperatures above about 70° C. U.S. Pat. No. 6,30,351 discloses a process for the production of N-(phosphonomethyl)iminodiacetic acid in an amidocarboxymethylation reactor system, into which a source of each of the following is continuously fed: (1) acetamide or an acetamide derivative, (2) formaldehyde or a formaldehyde generator of derivative, (3) a carbonylation catalyst, (4) carbon monoxide, and optionally (5) hydrogen. An amidocarboxymethylation reaction product stream, which contains N-(acetyl)iminodiacetic acid and the carbonylation catalyst, is withdrawn from the amidocarboxymethylation reactor system and the carbonylation catalyst is separated from the amidocarboxymethylation reaction product stream. The N-(acetyl)iminodiacetic acid is either: (1) reacted with a source of phosphorous and a source of formaldehyde in the presence of an acid to form a phosphonomethylation reaction product stream containing N-(phosphonomethyl)iminodiacetic acid and acetic acid; or (2) deacylated and cyclized to form a 2,5-diketopiperazine, and then reacted with a source of phosphorous and a source of formaldehyde in the presence of an acid to form a phosphonomethylation reaction product stream containing N-(phosphonomethyl)iminodiacetic acid and acetic acid.

WO 00/59915 describes a process for preparing PMIDA by neutralising a salt solution of IDA with sulphuric or hydrochloric acid, separating the IDA component e.g by filtration and conversion of IDA with formaldehyde and phosphorous acid in the presence of sulphuric or hydrochloric acid to thus yield PMIDA and possibly recirculating the filtrate. WO 96/40698 teaches a method for preparing PMIDA starting from IDA, a source of formaldehyde, a source of phosphorous acid and a source of strong acid, usually hydrochloric acid. This art process requires the infusion of phosphorous acid and formaldehyde at levels such that the level of phosphorous acid in the reaction mixture is reduced which will lead to the formation of undesirable by-products. $PCl_3$ is generally employed as the source of strong acid. WO 94/15939 also concerns a process for the manufacture of PMIDA starting from IDA with phosphorous acid and formaldehyde in an aqueous medium in the presence of concentrated sulphuric acid. PMIDA precipitates and can be filtered off and the filtrate can be recirculated to the reaction medium.

U.S. Pat. No. 6,232,494 concerns an improved process for the manufacture of glyphosate including a recitation of leading PMIDA making methods and inherent difficulties such as dealing with hindering sodium chloride levels and also a summary listing of difficulties to be overcome in converting PMIDA to glyphosate. The removal of chloride from PMIDA is also described in US 2002/0148786; the use of evaporative crystallisation constitutes a contemplated approach. U.S. Pat. No. 4,775,498 explains a method for the manufacture of N,N-diacetic acid aminoalkylene phosphonic acid (PAIDA) by addition of phosphorous trichloride to water and IDA, adding formaldehyde and water to dissolve alkali metal salt, followed by adjusting the pH and filtering the PMIDA precipitate. EP-A 0 595 598 illustrates a process for preparing PMIDA whereby IDA is first reacted with formaldehyde to yield HMIDA which component is subsequently reacted with phosphorous acid and so converted to PMIDA.

EP-A 0 679 158 describes a process for preparing PMIDA by reacting IDA with phosphorous acid and formaldehyde in the presence of concentrated sulphuric or hydrochloric acid and recovering the PMIDA precipitate. EP-A 0 618 212 similarly describes a process for preparing PMIDA by reacting IDA with formaldehyde and an aqueous solution of phosphorous acid and hydrochloric acid, resulting from the phosphorous trichloride hydrolysis. The PMIDA can then be recovered from the reaction product. GB 2 154 589 concerns an energy economic arrangement for preparing PMIDA starting from IDA species, sulfuric acid and hydrochloric acid. CN 101348266 relates to the treatment of the NaCl containing PMIDA mother liquid to thus recover the PMIDA and utilize the NaCl by-product. CN 101307074 pertains to a method for preparing PMIDA and chloroalkane and acetal by-products. CN 101284847 describes the making of PMIDA by reacting IDA Na salts with sulphuric acid at pH 5-8 and mixing the IDA so formed with phosphorous acid and formaldehyde to thus yield PMIDA. WO 2009/130322 describes a process for the manufacture of amino alkylene phosphonic acids starting from $P_4O_6$ in the presence of a homogeneous Broensted catalyst. The method can be used for the preparation of PMIDA.

The prior art abundantly illustrates the significant difficulties and shortcomings attached to the use of known PMIDA manufacturing technologies. Major difficulties can reside in the selection of the acid catalyst, usually sulphuric and/or hydrochloric acid, the presence of chlorides, frequently alkali chlorides, the formation of undesirable levels of by-products and the lack of selectivity of the reaction product. In addition, PMIDA produced in accordance with art technologies, requires special precautions in the conversion to glyphosate while the corrosive nature of chloride ions can adversely affect equipment economics.

While considerable moneys have been spent for the purpose of alleviating quality and/or economic aspects of the manufacturing technology, marginal solutions directed to specific shortcomings have, at best, been achieved.

It is an aim of this invention to make available a manufacturing arrangement which does not require the use of a concentrated acid, such as hydrochloric acid and does not require on-purpose purification of the end product. Still another object of the invention aims at providing the end product in a reactant uniform medium whereby the mother liquid can easily be recycled. Still another object pertains at avoiding using corrosive reactants. Another major object of the invention contemplates synthesizing the end product, routinely recoverable, and recycling the mother liquid, without any further treatment into the reaction. Yet another object of the invention aims at providing a PMIDA manufacturing arrangement proceeding with significantly reduced conversion of phosphorous acid to phosphoric acid. Yet another object of the invention concerns a manufacturing arrangement capable of yielding end products with significantly reduced levels of undesirable by-products such as N-methyl iminodiacetic acid and/or HO—$CH_2PO_3H_2$. It is a major object of this invention to provide a PMIDA manufacturing method which is not affected by the cumulative art shortcomings and which can yield a high purity product.

The term "percent" or "%" as used throughout this application stands, unless defined differently, for "percent by weight" or "% by weight". The terms "phosphoric acid" and "phosphonate" are also used interchangeably depending, of course, upon medium prevailing alkalinity/acidity conditions. The term "Ppm" stands for "parts per million". The terms "$P_2O_3$" and "$P_4O_6$" can be used interchangeably. Unless defined differently, pH values are measured at 25° C. on the reaction medium as such. The designation "phosphorous acid" means phosphorous acid as such, phosphorous acid prepared in situ starting from $P_4O_6$ or purified phosphorous acid starting from $PCl_3$ or purified phosphorous acid resulting from the reaction of $PCl_3$ with carboxylic acid, sulfonic acid or alcohol to make the corresponding chloride. The term "phosphoric acid" embraces aqueous solutions of that acid and phosphoric acid prepared in situ starting from $P_2O_5$. The term "formaldehyde" designates interchangeably formaldehyde sensu stricto, aldehydes and ketones, preferably formaldehyde sensu stricto. The term "$P_4O_6$" embraces neat $P_4O_6$ in the liquid state, solid $P_4O_6$ and gaseous $P_4O_6$. The term "ambient" with respect to temperature and pressure means terrestrial conditions usually prevailing at sea level, i.e., temperature is about 18° C.-25° C. and pressure stands for 1319.891-1399.885 hPa(990-1050 mm Hg). The term "substantially insoluble in the reaction medium" preferably means that the phosphonoalkyliminodiacetic acid has a solubility of no more than 10 g/100 g of reaction medium, more preferred 1 g/100 g of reaction medium, measured at ambient temperature and pressure. The solubility is determined at the pH of the reaction medium, preferably below 2, more preferably below 1.

The above and other objects can now be attained by means of a method arrangement whereby an iminodiacetic acid is reacted with an about stoichiometric amount of phosphorous acid in the presence of a fairly substantial level of phosphoric acid, namely in a molar ratio of phosphoric acid:phosphorous acid of 9:0.8 to 1:1. In more detail, this invention pertains to a method for the manufacture of a phosphonoalkyl iminodiacetic acid having the formula:

$$M_2PO_3—X—N—(CH_2COOM)_2$$

wherein X is a $C_{1-6}$ linear or branched alkylene group; and M is selected from hydrogen, alkali, earth-alkali, ammonium and protonated amine; comprising a) reacting iminodiacetic acid with phosphorous acid whereby the phosphorous acid is used in a molar ratio of phosphorous acid:iminodiacetic acid of from 0.7:1 to 1.5:1 in the presence of phosphoric acid whereby the molar ratio of phosphoric acid:phosphorous acid is of from 9:0.8 to 1:1 and formaldehyde at a temperature in the range of from 45° C. to 200° C. for a period of from 1 minute to 10 hours, to thereby yield a substantially medium insoluble reaction product;

b) separating the insoluble reaction product from the reaction medium, and optionally water washing the insoluble reaction product.

In a preferred execution herein, the alkylene group is a $C_1$-$C_4$ alkylene group, in particular methylene, and the end product, PMIDA, can easily be converted to glyphosate, a well known herbicide commercialized for already several decades.

In another preferred embodiment herein, the phosphorous acid is prepared in situ starting from, preferably liquid, $P_4O_6$.

The claimed technology is particularly beneficial in that the system operates under exclusion of system-foreign components with its obviously significant benefits. However, it is understood that the reaction in accordance with this invention, i.e. reacting iminodiacetic acid with phosphorous acid and formaldehyde in the presence of an acid catalyst, will usually yield a low level of phosphoric acid. Phosphoric acid is within the context of this invention considered as a quasi-system component considering, inter alia, the fact that after the separation of the reaction product, the remaining part of the reaction medium, i.e. the mother liquid, can generally be recycled easily. In some cases the insolubility of the reaction product can be enhanced by adding water and/or a water-soluble organic diluent. So proceeding requires routine measures well known in the domain of separation technology. Examples of suitable organic diluents include alcohols e.g. ethanol and methanol. The levels of the precipitation additives e.g. water/alcohol to be used vary based on the reaction medium and can be determined routinely. It goes without saying that the organic diluent can desirably be removed, e.g. by distillation, before the mother liquid is recycled.

The insoluble amino alkylene phosphonic acid reaction product can be separated from the liquid phase, e.g. for recovery purposes, by physical means known in the art e.g. by settling, filtration or expression. Examples of the like processes include gravity settling sometimes through exercising centrifugal force e.g. in cyclones; screen, vacuum or centrifugal filtration; and expression using batch or continuous presses e.g. screw presses.

If desired, the separated reaction product can be further purified by known methods, such as re-crystallization or chromatography.

The phosphorous acid reactant is a commodity material well known in the domain of the technology. It can be prepared, for example, by various technologies some of which are well known, including hydrolysing phosphorus trichloride or P-oxides. Phosphorous acid and the corresponding P-oxides can be derived from any suitable precursor including naturally occurring phosphorus containing rocks which can be converted, in a known manner, to elemental phosphorus followed by oxidation to P-oxides and possibly phosphorous acid. The phosphorous acid reactant can also be prepared, starting from hydrolyzing $PCl_3$ and purifying the phosphorous acid so obtained by eliminating hydrochloric acid and other chloride intermediates originating from the hydrolysis. In another approach, phosphorous acid can be manufactured beneficially by reacting phosphorus trichloride with a reagent which is either a carboxylic acid or a sulfonic acid or an alcohol. The $PCl_3$ reacts with the reagent under formation of phosphorous acid and an acid chloride in the case of an acid reagent or a chloride, for example an alkyl-chloride, originating from the reaction of the $PCl_3$ with the corresponding alcohol. The chlorine containing products, e.g. the alkylchloride and/or the acid chloride, can be conveniently separated from the phosphorous acid by methods known in the art e.g. by distillation. While the phosphorous acid so manufactured can be used as such in the claimed arrangement, it can be desirable and it is frequently preferred to purify the phosphorous acid formed by substantially eliminating or diminishing the levels of chlorine containing products and non-reacted raw materials. Such purifications are well known and fairly standard in the domain of the relevant manufacturing technology. Suitable examples of such technologies include the selective adsorption of the organic impurities on activated carbon or the use of aqueous phase separation for the isolation of the phosphorous acid component. Information pertinent to the reaction of phosphorous trichloride with a reagent such as a carboxylic acid or an alcohol can be found in Kirk-Othmer, Encyclopedia of Chemical Technology, in chapter Phosphorous Compounds, Dec. 4, 2000, John Wiley & Sons Inc.

In general, the method of the invention is conducted in the presence of not more than 2000 ppm of chlorine, preferably 400 ppm or less, in particular 200 ppm or less of chlorine, expressed in relation to the phosphorous acid component (100%).

In a preferred embodiment, the phosphorous acid reactant can be prepared by adding $P_4O_6$ to the reaction medium. The reaction medium can possibly contain the iminodiacetic acid, or the iminodiacetic acid can be added simultaneously with the $P_4O_6$. The iminodiacetic acid can also be added to the reaction medium after the hydrolysis of the $P_4O_6$ has been completed before the formaldehyde addition. In any case, the balance of the phosphoric acid is added before the formaldehyde addition. The simultaneous addition of the iminodiacetic acid and the $P_4O_6$ shall preferably be effected in parallel i.e. a premixing, before adding to the reaction medium, of the iminodiacetic acid and the $P_4O_6$ shall for obvious reasons be avoided.

In the method of the invention, the phosphorous acid shall be used in substantially stoichiometric proportions such as a molar ratio of phosphorous:iminodiacetic acid of from 0.7:1 to 1.5:1, preferably of from 0.8:1 to 1.3:1, in particular 0.9:1 to 1.1:1. The reaction is conducted in the presence of a substantial level of phosphoric acid in a molar ratio of phosphoric:phosphorous of from 9:0.8 to 1:1, preferably of from 6:1 to 1.2:1, in particular of from 4:1 to 1.5:1. The formaldehyde is used in the method of this invention in a molar ratio of formaldehyde:iminodiacetic acid of from 2:1 to 0.5:1; preferably from 1.5:1 to 0.7:1, in particular from 1.2:1 to 0.9:1. The use of relatively minor ratios of formaldehyde were found to be beneficial for optimizing selectivity while the non-reacted part of the raw material (mother liquid) can be recycled conveniently. The use of phosphoric acid actually promotes maximizing the efficiency of the reactants and thus the selectivity and yield of the end product. This constitutes a considerable step forward in the domain of the technology on account of purification and separation methods currently required in the application of the art technology.

In the preferred embodiment, the $P_4O_6$ can be represented by a substantially pure compound containing at least 85%, preferably more than 90%; more preferably at least 95% and in one particular execution at least 97% of the $P_4O_6$. While tetraphosphorus hexa oxide, suitable for use within the context of this invention, can be manufactured by any known technology, in preferred executions the hexa oxide can be prepared in accordance with the process disclosed in WO 2009/068636 A1 entitled "Process for the manufacture of $P_4O_6$" In detail, oxygen, or a mixture of oxygen and inert gas, and gaseous or liquid phosphorus are reacted in essentially stoichiometric amounts in a reaction unit at a temperature in the range from 1600 to 2000 K, by removing the heat created by the exothermic reaction of phosphorus and oxygen, while maintaining a preferred residence time of from 0.5 to 60 seconds followed by quenching the reaction product at a temperature below 700 K and refining the crude reaction product by distillation. The hexa oxide so prepared is a pure product containing usually at least 97% of the oxide. The $P_4O_6$ so produced is generally represented by a liquid material of high purity containing in particular low levels of elementary phosphorus, $P_4$, preferably below 1000 ppm, expressed in relation to the $P_4O_6$ being 100%. The preferred residence time is from 5 to 30 seconds, more preferably from 8 to 30 seconds.

The reaction product can, in one preferred execution, be quenched to a temperature below 350 K.

The term "$P_4O_6$" embraces, as spelled out, any aggregation state of the $P_4O_6$. However, it is presumed that the $P_4O_6$ participating in a reaction at a temperature of from 45° C. to 200° C. is necessarily liquid or gaseous although solid species can, academically speaking, be used in the preparation of the reaction medium.

The $P_4O_6$ (mp. 23.8° C.; bp. 173° C.), preferably in liquid form, is added to the aqueous reaction medium:
  preferably containing part of the phosphoric acid sufficient to maintain the pH below 5, preferably below 3, in particular equal to or smaller than 2 to thus complete the addition/hydrolysis of the $P_4O_6$ followed by the addition of the IDA and the remaining phosphoric acid; or
  containing the IDA component and part of the phosphoric acid sufficient to maintain the pH, at all times, below 5, preferably below 3, in particular equal to or smaller than 2
  simultaneously with the IDA which reaction medium preferably containing the phosphoric acid, provided that the pH of the reaction is kept, at all times, below 5, preferably below 3, in particular equal to or smaller than 2.

The reaction medium thus contains the $P_4O_6$ hydrolysate and the IDA, possibly as a salt. The hydrolysis is conducted at temperature conditions of 20° C. up to about 150° C. While higher temperatures e.g. up to 200° C., or even higher, can be used such temperatures generally require the use of an autoclave or can be conducted in a continuous manner, possibly under autogenous pressure built up. The temperature increase during the $P_4O_6$ addition can result from the exothermic hydrolysis reaction and was found to provide temperature conditions to the reaction mixture as can be required for the reaction with formaldehyde. If the $P_4O_6$ hydrolysis is conducted in the presence of the IDA, i.e. the IDA is present in the reaction medium before adding the $P_4O_6$, or if the IDA is added simultaneously with the $P_4O_6$, then the pH conditions recited above shall be strictly observed.

The $P_4O_6$ (mp. 23.8° C.; bp. 173° C.) in liquid form is added to the aqueous reaction medium containing, as described above, preferably part of the phosphoric acid, or the $P_4O_6$ is added simultaneously with the IDA to the reaction medium containing the phosphoric acid, subject to specific pH provisions, namely having a pH at all times below 5, preferably below 3, in particular equal to or smaller than 2. The $P_4O_6$ is added to the reaction mixture under stirring generally starting at ambient temperature, preferably at a temperature higher than 45° C.

The essential formaldehyde component is a well known commodity ingredient. Formaldehyde sensu stricto known as oxymethylene having the formula $CH_2O$ is produced and sold as water solutions containing variable, frequently minor, e.g. 0.3-3%, amounts of methanol and are typically reported on a 37% formaldehyde basis although different concentrations can be used. Formaldehyde solutions exist as a mixture of oligomers. Such formaldehyde precursors can, for example, be represented by paraformaldehyde, a solid mixture of linear poly(oxymethylene glycols) of usually fairly short, n=8–100, chain length, and cyclic trimers and tetramers of formaldehyde designated by the terms trioxane and tetraoxane respectively.

The formaldehyde component can also be represented by aldehydes and ketones having the formula $R_1R_2C=O$ wherein $R_1$ and $R_2$ can be identical or different and are selected from the group of hydrogen and organic radicals. When $R_1$ is hydrogen, the material is an aldehyde. When both $R_1$ and $R_2$ are organic radicals, the material is a ketone. Species of useful aldehydes are, in addition to formaldehyde, acetaldehyde, caproaldehyde, nicotinealdehyde, crotonaldehyde, glutaraldehyde, p-tolualdehyde, benzaldehyde, naphthaldehyde and 3-aminobenzaldehyde. Suitable ketone species for use herein are acetone, methylethylketone, 2-pentanone, butyrone, acetophenone and 2-acetonyl cyclohexanone.

The reaction in accordance with this invention is conducted in a manner routinely known in the domain of the technology. As illustrated in the experimental showings, the method can be conducted by combining the essential reaction partners and heating the reaction mixture to a temperature usually within the range of from 45° C. to 200° C., and higher temperatures if elevated pressures are used, more preferably 70° C. to 150° C., generally for a period of 1 minute to 10 hours, in one preferred execution from 100° C. to 150° C. for a a period of 15 minutes to 4 hours. The upper temperature limit actually aims at preventing any substantially undue thermal decomposition of the phosphorous acid reactant. It is understood and well known that the decomposition temperature of the phosphorous acid, and more in general of any other individual reaction partners, can vary depending upon additional physical parameters, such as pressure and the qualitative and quantitative parameters of the ingredients in the reaction mixture.

The inventive method can be conducted under substantial exclusion of added water—meaning in the preferred embodiment beyond the stoichiometric level required for the hydrolysis of the $P_4O_6$. However, it is understood that the reaction in accordance with the inventive method, i.e. the formation of N—C—P bonds, will generate water. After the $P_4O_6$ hydrolysis has been completed, the amount of residual water is such that the weight of water is from 0% to 60% expressed in relation to the weight of iminodiacetic acid It is understood that the claimed technology is particularly beneficial in that the system operates under exclusion of system-foreign components with its obviously significant benefits. Phosphoric acid is within the context of this invention considered as a quasi-system component considering, inter alia, the fact that after the separation of the reaction product, the remaining part of the reaction medium, i.e. the mother liquid, can generally be recycled easily. In some cases the insolubility of the reaction product can be enhanced by adding water and/or a water-soluble organic diluent. So proceeding requires routine measures well known in the domain of separation technology. Examples of suitable organic solvents include alcohols e.g. ethanol and methanol. The levels of the precipitation additives e.g. water/alcohol to be used vary based on the reaction medium and can be determined routinely. It goes without saying that the organic solvents shall be removed, e.g. by distillation, before the mother liquid is recycled.

The insoluble amino alkylene phosphoric acid reaction product can be separated from the liquid phase, e.g. for recovery purposes, by physical means known in the art e.g. by settling, filtration or expression. Examples of the like processes include gravity settling sometimes through exercising centrifugal force e.g. in cyclones; screen, vacuum or centrifugal filtration; and expression using batch or continuous presses e.g. screw presses.

The inventive reaction can be conducted at ambient pressure and, depending upon the reaction temperature, under distillation of water, thereby also eliminating a minimal amount of non-reacted formaldehyde. The duration of the reaction can vary from virtually instantaneous, e.g. 1 minute, to an extended period of e.g. 10 hours. This duration generally includes the gradual addition, during the reaction, of formaldehyde and possibly other reactants. In one method set up, the phosphorous acid, the IDA and the phosphoric acid are added to the reactor followed by heating this mixture under gradual addition of the formaldehyde component starting at a temperature e.g. in the range of from 45° C. to 150° C. This reaction can be carried out under ambient pressure with or without distillation of usually water and some non-reacted formaldehyde.

In another operational arrangement, the reaction can be conducted in a closed vessel under autogenous pressure built up. In this method, the reaction partners, in total or in part, are added to the reaction vessel at the start. In the event of a partial mixture, the additional reaction partner can be gradually added, alone or with any one or more of the other reaction partners, as soon as the effective reaction temperature has been reached. The formaldehyde reactant can, for example, be added gradually during the reaction alone or with parts of the amine or the phosphorous acid.

In yet another operational sequence, the reaction can be conducted in a combined distillation and pressure arrangement. Specifically, the reaction vessel containing the reactant mixture is kept under ambient pressure at the selected reaction temperature. The mixture is then, possibly continuously, circulated through a reactor operated under autogenous (autoclave principle) pressure built up thereby gradually adding the formaldehyde or additional reaction partners in accordance with needs. The reaction is substantially completed under pressure and the reaction mixture then leaves the closed vessel and is recirculated into the reactor where distillation of water and other non-reacted ingredients can occur depending upon the reaction variables, particularly the temperature.

The foregoing process variables thus show that the reaction can be conducted by a variety of substantially complementary arrangements. The reaction can thus be conducted as a batch process by heating the initial reactants, usually the phosphorous acid, the IDA and the phosphoric acid in a (1) closed vessel under autogenous pressure built up, or (2) under reflux conditions, or (3) under distillation of water and minimal amounts of non-reacted formaldehyde, to a temperature preferably in the range of from 70° C. to 150° C. whereby the formaldehyde component is added, as illustrated in the Examples, gradually during the reaction. In a particularly preferred embodiment, the reaction is conducted in a closed vessel at a temperature in the range of from 100° C. to 150° C., coinciding particularly with the gradual addition of formaldehyde, within a time duration of from 1 minute to 30 minutes, in a more preferred execution from 1 minute to 10 minutes.

In another approach, the reaction is conducted as a continuous process, possibly under autogenous pressure, whereby the reactants are continuously injected into the reaction mixture, at a temperature preferably in the range of from 70° C. to 150° C. and the phosphonic acid reaction product is withdrawn on a continuous basis.

In yet another arrangement, the method can be represented by a semi-continuous set-up whereby the phosphonic acid reaction is conducted continuously whereas preliminary reactions between part of the components can be conducted batch-wise.

The reaction product can subsequently, and in accordance with needs, be neutralized, in part or in total, with a base, preferably ammonia, amines, alkali hydroxides, earth-alkali hydroxides or mixtures thereof It is understood that the claimed technology is particularly beneficial in that the reaction medium is uniform and that the reaction partners are identical to the constituents of the products to be manufactured i.e. the system operates under exclusion of system-foreign components with its obviously significant benefits. This includes, inter alia, the fact that after the separation of the reaction product, the remaining part of the reaction medium, i.e. the mother liquid, can generally be recycled easily. In some cases the insolubility of the reaction product can be enhanced by adding water and/or a water-soluble organic diluent. So proceeding requires routine measures well known in the domain of separation technology. Examples of suitable organic solvents include alcohols e.g. ethanol and methanol. The levels of the precipitation additives e.g. water/alcohol to be used vary based on the reaction medium and can be determined routinely.

It goes without saying that the organic solvents shall be removed, e.g. by distillation, before the mother liquid is recycled.

The invention is illustrated by example syntheses as follows, without limiting it thereby.

EXAMPLES

Example 1

In a three-necked round-bottom flask equipped with a mechanical stirrer, 33.28 g (0.25 mol) of iminodiacetic acid (IDA) were mixed with 20.5 g (0.25 mol, 1 eq.) of phosphorous acid and 122.5 g (1.25 mol, 5 eq.) of phosphoric acid. The reaction mixture was heated to 140° C. 20.68 ml of 36.6 wt.-% aqueous solution of formaldehyde (1.1 eq.) were then added over 60 min. During the addition, the temperature of the reaction mixture decreased from 140° C. to 125° C. At the end of the formaldehyde addition the reaction mixture was kept at reflux for 30 min. The precipitate formed by cooling the reaction mixture was isolated by filtration and washed with fresh water. After drying the precipitate was analysed by $^1$H and $^{31}$P NMR and identified as 81.3% pure N-(phosphonomethyl)iminodiacetic acid (PMIDA, 28 g, 61.2% yield).

Example 2

In a three-necked round-bottom flask equipped with a mechanical stirrer, 33.28 g (0.25 mol) of iminodiacetic acid (IDA) were mixed with 20.5 g (0.25 mol, 1 eq.) of phosphorous acid, 122.5 g (1.25 mol, 5 eq.) of phosphoric acid and 13.6 g of water. The reaction mixture was heated to 130° C. 18.80 ml of 36.6 wt.-% aqueous solution of formaldehyde (1 eq.) were then added over 118 min. During the addition, the temperature of the reaction mixture decreased from 130° C. to 124° C. At the end of the formaldehyde addition the reaction mixture was kept at reflux for 30 min. The precipitate formed by cooling the reaction mixture was isolated by filtration and washed with fresh water. After drying precipitate was analysed by H and $^{31}$P NMR and identified as 94.4% pure N-(phosphonomethyl)iminodiacetic acid (PMIDA, 39.7 g, 79.5% yield).

Example 3

In a three-necked round-bottom flask equipped with a mechanical stirrer, 33.28 g (0.25 mol) of iminodiacetic acid (IDA) were mixed with 20.5 g (0.25 mol, 1 eq.) of phosphorous acid, 122.5 g (1.25 mol, 5 eq.) of phosphoric acid and 13.6 g of water. The reaction mixture was heated to 140° C. 18.80 ml of 36.6 wt.-% aqueous solution of formaldehyde (1 eq.) were then added over 118 min. During the addition, the temperature of the reaction mixture decreased from 140° C. to 130° C. At the end of the formaldehyde addition the reaction mixture was kept at reflux for 30 min. The precipitate formed by cooling the reaction mixture was isolated by filtration and washed with fresh water. The dried precipitate was analysed by H and $^{31}$P NMR and identified as 91.4% pure N-(phosphonomethyl) iminodiacetic acid (PMIDA, 35.3 g, 71.7% yield).

The invention claimed is:

1. A method for the manufacture of a phosphonomethyl iminodiacetic acid or a salt thereof having the formula:

M2PO3—CH2—N—(CH2COOM)2

Wherein M is selected from hydrogen, alkali, earth-alkali, ammonium and protonated amine; comprising the steps of:
  a) reacting iminodiacetic acid with phosphorous acid whereby the phosphorous acid is used in a molar ratio of phosphorous acid: iminodiacetic acid of from 0.7:1 to 1.5:1 in the presence of phosphoric acid whereby the molar ratio of phosphoric acid: phosphorous acid is of from 9:0.8 to 1:1 and formaldehyde in a molar ratio formaldehyde: iminodiacetic acid of from 2:1 to 0.5:1, at a temperature in the range of from 45° C. to 200° C. for a period of from 1 minute to 10 hours, to thereby yield a substantially reaction medium insoluble product;
  b) separating the insoluble reaction product from the reaction medium, and optionally water washing the insoluble reaction product, wherein the mother liquid is, after the separation of the reaction product, recycled into the reaction medium, wherein the term "phosphoric acid" means phosphoric acid prepared in situ starting from P2O5, with the proviso that hydrochloric acid is not present in the reaction medium.

2. The method in accordance with claim 1 wherein the molar ratio of phosphoric acid: phosphorous acid is from 6:1 to 1.2:1 and wherein the molar ratio of phosphorous acid: iminodiacetic acid is from 0.8:1 to 1.3:1.

3. The method in accordance with claim 2 wherein the molar ratio of phosphoric: phosphorous is from 4:1.5 to 1.2:1 and wherein the molar ratio of phosphorous:
iminodiacetic acid is from 0.9: to 1.1:1.

4. The method in accordance with claim 1 wherein the molar ratio of formaldehyde: iminodiacetic acid is from 1.5:1 to 0.7:1.

5. The method in accordance with claim 1 wherein the reaction is carried out at a temperature in the range of from 70 ° C. to 150 ° C. combined with an approach selected from:

(A) conducting the reaction under ambient pressure with or without distillation of water and non-reacted formaldehyde;
(B) conducting the reaction in a closed vessel under autogenous pressure built up;
(C) conducting the reaction in a combined distillation and pressure arrangement whereby the reaction vessel containing the reaction mixture is kept under ambient pressure at the reaction temperature followed by circulating the reaction mixture through a reactor operated under autogenous pressure built up thereby gradually adding the formaldehyde and other reactants; and
(D) a continuous process arrangement, optionally under autogenous pressure built up, whereby the reactants are continuously injected into the reaction mixture and the phosphonic acid reaction product is withdrawn on a continuous basis.

6. The method in accordance with claim 1 wherein:
the molar ratio of phosphoric: phosphorous is from 6:1 to 2:1;
the molar ratio of formaldehyde: iminodiacetic acid is from 1.3:1 to 0.8:1;
the temperature is from 100° C. to 150° C.; and
the duration (period) is from 10 minutes to 4 hours.

7. The method in accordance with claim 6 wherein:
the molar ratio of phosphoric: phosphorous is from 5:1 to 3:1;
the molar ratio of phosphorous: iminodiacetic acid is from 1.1:1 to 0.9:1;
the molar ratio of formaldehyde: iminodiacetic acid is from 0.9: 1 to 1.1:1;
the temperature is from 110 ° C. to 140 ° C.; and
the duration (period) is from 30 minutes to 2 hours.

8. The method in accordance with claim 1 wherein the level of chlorine in the reaction medium is 2000 ppm or less, expressed in relation to the phosphorous acid (100%).

9. The method in accordance with claim 8 wherein the level of chlorine in the reaction medium is less than 400 ppm of chlorine expressed in relation to the phosphorous acid (100%).

10. The method in accordance with claim 9 wherein the level of chlorine in the reaction medium is less than 200 ppm of chlorine expressed in relation to the phosphorous acid (100%).

11. The method in accordance with claim 1 wherein the phosphorous acid is prepared in situ by adding $P_4O_6$ to an aqueous reaction medium:
  (a) containing phosphoric acid in a level to maintain the pH in the reaction medium below 5, whereby the reaction medium contains in addition to the water and the phosphoric acid the iminodiacetic acid; or
  (b) containing the iminodiacetic acid and the phosphoric acid to maintain the pH, at all times, below 5; or
  (c) simultaneously with the iminodiacetic acid provided the pH of the reaction medium is maintained, at all times, below 5.

12. The method in accordance with claim 11 wherein the $P_4O_6$ is manufactured by reacting oxygen and phosphorus in essentially stoichiometric amounts in a reaction unit at a temperature in the range of from 1600 to 2000 K with a reaction residence time from 0.5 to 30 seconds, followed by quenching the reaction product at a temperature below 700 K and refining the reaction product by distillation.

13. The method in accordance with claim 12 wherein the level of elementary phosphorus in the $P_4O_6$ is below 1000 ppm, expressed in relation to $P_4O_6$ (100%).

* * * * *